United States Patent [19]

Burstein

[11] Patent Number: 5,571,513
[45] Date of Patent: Nov. 5, 1996

[54] ANTI-GP130 MONOCLONAL ANTIBODIES

[75] Inventor: Samuel A. Burstein, Edmond, Okla.

[73] Assignee: The Board Of Regents Of The University Of Oklahoma, Norman, Okla.

[21] Appl. No.: 455,799

[22] Filed: May 31, 1995

[51] Int. Cl.$^6$ .................. A61K 39/395; C07K 16/28; C12P 21/08; C12N 5/20
[52] U.S. Cl. .................. 424/144.1; 424/153.1; 424/173.1; 435/70.21; 435/172.2; 435/240.27; 530/387.1; 530/388.22; 530/388.7; 530/388.85; 530/391.3; 530/389.6
[58] Field of Search .................. 424/130.1, 144.1, 424/153.1, 173.1, 93.71; 435/70.21, 172.2, 240.27; 530/387.1, 388.22, 388.7, 388.85, 391.3, 389.6

[56] References Cited

PUBLICATIONS

Nishimoto et al. (1994) J. Exp. Mad. 179 1343–1347.
Tamura et al. (1993) Proc. Natl. Acad. Sci USA 90 11924–11928.
Yasukawa et al. (1992) Immunol. Letters 31 123–130.
Hibi et al. (1990) Cell 63 1149–1157.
Galfré (1981). Methods in Enzymology 73 1–46.
Mackiewicz et al., "Complex of Soluble Human IL–6–Receptor/IL–6 Up–Regulates Expression of Acute–Phase Proteins", *The Journal of Immunology*, vol. 149, 2021–2027, Sep. 15, 1992.
Taga et al., "Functional Inhibition of Hematopoietic and Neurotrophic Cytokines by Blocking the Interleukin 6 Signal Transducer gp130", *Proc. Natl. Acad. Sci. USA*, vol. 89, 10998–11001, Nov. 1992.
Narazaki et al., "Soluble Forms of the Interleukin–6 Signal–Transducing Receptor Component gp130 in Human Serum Possessing a Potential to Inhibit Signals Through Membrane–Anchored gp130", *Blood*, vol. 82, No. 4, 1120–1126, Aug. 15, 1992.
Wendling et al., "Treatment of Severe Rheumatoid Arthritis By Anti–Interleukin 6 Monoclonal Antibody", *The Journal of Rheumatology*, 20:259–262, 1993.
Saito et al., "Preparation of Monoclonal Antibodies Against the IL–6 Signal Transducer, gp130, That Can Inhibit IL–6–mediated Functions", *Journal of Immunological Methods*, 163:217–223, 1993.

*Primary Examiner*—Robert D. Budens
*Assistant Examiner*—Julie E. Reeves
*Attorney, Agent, or Firm*—Dunlap & Codding, P.C.

[57] ABSTRACT

Anti-gp130 monoclonal antibodies (Mabs) obtained from hybridomas designated 4B11 and 2H4 are effective in the inhibition of the acute phase response on hepatoma cells and prevent the IL-6-induced growth inhibition of A375 cells in vitro. Administration of the antibodies to dogs showed that 2H4 is a potent in vivo inhibitor of the IL-6-induced acute phase response, abrogating IL-6-mediated-increments in fibrinogen, C-reactive protein and the platelet count. Antibodies may be used in methods for measuring soluble gp130 and in therapeutic treatments. The 2H4 antibody may be used in inhibiting in vivo the function of gp130 or cellular factors dependent on gp130 for cellular transduction.

4 Claims, 6 Drawing Sheets

ANTI-GP130 MONOCLONAL ANTIBODIES

This work was supported in part by NIH grant HL50059. The U.S. Government has certain rights in this invention.

BACKGROUND

The present invention is related to antibodies which specifically bind to the human gp130 receptor, hybridomas for producing such antibodies, and therapeutic uses of such antibodies to inactivate gp130 thereby treating diseases reliant on the gp130 receptor.

Interleukin 6 ( IL-6) is a multi-functional cytokine that exhibits a plethora of biological activities (Kishimoto, T., *Blood,* 1989, 74:1–10; van Snick, J., *Annu. Rev. Inununol.,* 1990, 8:253–278; Akira et al., 1993, *Adv. Immunol.,* 1993, 54:1–78). Among these are the induction of the hepatic acute phase response (Castell et al., *FEBS Lett.,* 1989, 242:237–239), B cell antibody production (Muraguchi et al., J. Exp. Med., 1988, 167:322–344), maturation of megakaryocytes (Ishibashi et al., *Proc. Natl. Acad. Sci. USA,* 1989, 86: 5953–5957) and augmentation of platelet production (Ishibashi et al., *Blood,* 1989, 74:1241–1244). A number of other cytokines including leukemia inhibitory factor [LIF (Metcalf, D., *Int. J. Cell Cloning,* 1991, 9:95–108)], oncostatin M (Rose et al., *Proc. Natl. Acad. Sci . USA,* 1991, 88:8641–8645) , ciliary neurotrophic factor [CNTF (Schooltink et al., *FEBS Lett.,* 1992, 314:280–284)] and interleukin 11 [IL-11 (Yonemura et al., *Br. J. Haematol.,* 1993, 84:16–23)] also mediate similar biological effects. This apparent functional redundancy can be explained since their cellular signals are all transduced via common receptor β chain subunit known as gp130 [CD130; (Kishimoto et al., *Cell,* 1994, 76:253–262; Taga et al., *Cell,* 1989, 58:573–581)]. Specificity is provided by the binding of the cytokine to its non-signal transducing α chain. Although this specific interaction is of relative low affinity, the cytokine-α chain binding facilitates interaction with gp130 to form a high affinity complex, resulting in dimerization and signal transduction.

Of this family of cytokines, IL-6 is the best characterized and has been studied in a variety of human diseases. Increased IL-6 production has been observed in inflammatory disorders, autoimmune diseases and cancer, and may be involved in their symptomatology and/or pathogenesis. Consequently, blocking the biological effects of IL-6 may have therapeutic utility in treatment of a number of disorders and diseases.

A number of different approaches to inhibiting IL-6 activity have been investigated. These include: (1) direct blockade of cytokine synthesis; (2) direct inhibition via anti-IL-6 antibodies; (3) inhibition of IL-6-mediated signal transduction via competition with various inactive IL-6 mutants; (4) inhibition of binding of IL-6 to the α chain of its receptor via anti-IL-6 receptor α antibodies; (5) inhibiting signal transduction with soluble forms of gp130; and (6) inhibition of signal transduction via anti-gp130 antibodies (Taga et al., *Proc. Natl. Acad. Sci. USA,* 1992, 89:10998–11001; Saito et al., *J. Immunol. Meth.,* 1993, 163:217–223). The latter approach is not specific for IL-6 and is potentially suitable for inhibiting the biological activity of other members of the gp130 signalling family of cytokines.

Anti-IL-6 and anti-IL-6R antibodies have both been reported to be effective inhibitors of IL-6 both in vitro and in vivo. Anti-IL-6 antibody administration blocks myeloma cell proliferation in vivo, attenuating the activation of coagulation in experimental endotoxemia and ameliorating symptomatic rheumatoid arthritis in man. Anti-IL-6R antibodies have also been shown to inhibit the biological effects of IL-6 in animal models including abrogation of the IL-6-induced augmentation of the platelet count. Another potential approach would be to specifically inhibit the IL-6/α chain interaction as recently shown with the soluble IL-1 receptor. However, soluble forms of the IL-6 receptor α chain have been shown to be agonists in this system since they are capable of binding to IL-6 and associating with cellular gp130 (Mackiewicz et al., *J. Immunol.,* 1992, 149:2021–2027). A novel approach has been the development of IL-6 mutants which inhibit the interaction of the IL-6/α chain complex with gp130 in vitro. Suramin has also been shown to inhibit IL-6 bioactivity in vitro and in vivo probably via non-specific receptor blockade or inhibition of signal transduction.

Although the potential role of the other cytokines of this family in the aforementioned disorders remains to be elucidated, blockade of the common gp130 subunit offers the possible advantage that one or more members of the IL-6 family of cytokines may be inhibited by a single specific antagonist. The efficacy of such an approach has been demonstrated in vitro with monoclonal antibodies (Mabs) raised against the extracellular domain of gp130 (Taga et al., *Proc. Natl. Acad. Sci. USA,* 1992, 89:10998–11001) as noted above.

Some cytokines such as IL-6 are crucial for the growth and development of certain malignant cells. Multiple myeloma for example, is a not uncommon malignancy in man in which inhibition of IL-6 by means of anti-IL-6 antibodies has been shown to ameliorate the disease process. IL-6 may be involved in the growth of lymphomas in patients with AIDS. The potential advantage for anti-gp130 therapy rather than specific anti-IL-6 therapy is that targeting this receptor molecule may inhibit not only IL-6 effects but also cell growth that may in part be mediated by other cytokines that share the gp130 pathway. For example, the cytokine oncostatin M which operates via gp130, has been implicated in the pathogenesis of Kaposi's sarcoma, a malignancy found in AIDS patients.

Since gp130 is a portion of the receptor for a number of cytokines that promote the acute phase response (including interleukin-11, leukemia inhibitory factor and oncostatin M), inhibition of that response with an antibody may well be employed as an anti-inflammatory agent, since the acute phase response is part of the inflammatory process.

Consequently, any disorder in which inflammation has a prominent component may be amenable to therapy. Common inflammatory disorders for which such therapies might be beneficial include rheumatoid arthritis, systemic lupus erythematosus and inflammatory bowel disease such as ulcerative coliris. Moreover, atherosclerosis and thrombotic disease may in part be related to inflammation. A therapy effective in targeting and inactivating the gp130 receptor would obviously be desired in the treatment of inflammatory disorders and other disorders or disease states which operate via the gp130 receptor.

DESCRIPTION OF THE INVENTION

The present invention contemplates monoclonal antibodies (Mabs) produced against the extracellular portion of the human gp130 molecule which bind to gp130 thereby blocking gp130 and inhibiting the effects of IL-6 or any cellular factor (such as a cytokine, which may in particular be IL-6, IL-11, oncostatin M, leukemia inhibitory factor, and ciliary neurotrophic factor, for example) dependent on gp130 for cellular transduction. The present invention also contemplates hybridomas which produce said antibodies. The present invention further comprises a method for treating a mammal to inhibit the acute phase component of inflammation or any disorder or disease state in a mammal which operates via the gp130 receptor.

The present invention further contemplates any method that results in detecting soluble gp130, such as may be found in a body fluid such as serum, plasma, cerebrospinal fluid, or any body fluid which may contain soluble gp130, by producing a detectable immunocomplex containing a substantially pure gp130 molecule or portion and an antibody of the present invention. Those skilled in the art will understand that there are numerous well known clinical diagnostic chemistry procedures that can be utilized to form these detectable complexes.

In particular, the present invention contemplates an antibody, and a composition comprising such an antibody, which specifically binds to the extracellular domain of human gp130 and which is produced by a hybridoma selected from one of 2H4 and 4B11, more particulary where the antibody is monoclonal. The antibody may be labeled with a detectable marker.

The hybridoma 2H4 was deposited with American Type Culture Collection (ATCC) located at 12301 Praklawn DR., Rockville, Md. 20852, on Jan. 17, 1996, and has ATCC Accession No. HB12022.

The invention further contemplates a hybridoma which produces antibody molecules that specifically bind to the extracellular domain of human gp130, including hybridomas selected from one of 2H4 and 4B11.

The present invention further contemplates a method of treating a mammal to inhibit the acute phase component of an inflammatory response, the method comprising administering to the mammal a composition comprising an effective amount of a monoclonal antibody obtained from the 2H4 hybridoma. Further contemplated is a method for blocking gp130 in vivo, comprising administering a composition comprising an effective amount of a monoclonal antibody obtained from the 2H4 hybridoma. Further contemplated is a method for inhibiting the function of a cellular factor dependent on gp130 signal transduction, comprising administering to a mammal a composition comprising an effective amount of a monoclonal antibody obtained from the 2H4 hybridoma.

Shown herein are the in vitro and in vivo biological activities of five anti-gp130 Mabs. The antibody-producing hybridomas described herein are 3F7, 2H4, 1G1, 4B11 and 5A8. Each hybridoma produces, respectively, Mab 3F7, Mab 2H4, Mab 1G1, Mab 4B11 and Mab 5A8. The five Mabs are shown to exhibit variable degrees of inhibition of the biological activities of IL-6, oncostatin M and IL-11 on hepatoma (Hep 3B) and melanoma cells (A375). These results confirm that gp130 is indeed the common signal transducer for the IL-6 family of cytokines. There is variability in the capacity of the different Mabs to inhibit in vitro bioactivity on human cell lines, as shown herein. Two of the Mabs (2H4 and 4B11) were evaluated in vivo in a canine model with short-term administration of IL-6 (in which exogenous administration of this IL-6 is used to simulate disease-related endogenous elevations of the cytokine). Thus, to determine the in vivo efficacy of the Mabs, the work shown herein focused on the potential to inhibit IL-6-induced augmentation in fibrinogen and CRP levels in peripheral blood.

The approach employed herein, as described in more detail below, was to infuse antibodies beginning 24 hours before commencement of IL-6 infusion in an effort to occupy gp130 receptor sites with antibody prior to exposure to IL-6. Antibody infusion was continued for 3–4 days and IL-6 for 10 days. The results provided below clearly show that 2H4 is an effective in vivo inhibitor of the acute phase response induced by IL-6 at the dose of 40 µg/kg/day (IL-6 has been administered to man in phase 1 studies in doses that usually have been <30 µg/kg/day). The antibody was capable of not only significantly abrogating the observed rise in both CRP and fibrinogen levels in the short term, but also delaying the IL-6-induced augmentation of the platelet count. Measurement of circulating levels of antibody suggest that the dosage was in excess of concentrations (10 µg/ml) required in vitro to inhibit the cellular response to IL-6, assuming that blood levels are in some measure reflective of tissue concentrations.

This study demonstrates that anti-gp130 Mabs can be employed to inhibit the function of gp130 and thereby the biological activity of gp130-signalling cytokines, in vitro, and in vivo. Use of these or similar reagents may be used as therapies to inhibit or ameliorate the acute phase component of the inflammatory response in inflammatory disorders.

The following examples are intended to illustrate, but not limit, the present invention.

Methods

Animals

Beagles (Hazleton Research Products, Cumberland Va.) (8–13 kg) were obtained and housed according to the regulations of the Institutional Animal Care and Use Committee of the University of Oklahoma Health Sciences Center.

Cytokines

Recombinant human IL-6 was expressed in *Escherichia coli* and purified as described in (Burstein et al., Blood, 1992, 80:420–428. Concentration and purity were assessed by the IL-6-responsive B9 cell line bioassay and SDS-PAGE. Endotoxin levels were measured with the limulus amebocyte lysate test at Endosafe Inc., Charleston, S.C. The specific activity was 2–5×10$^8$ U/mg protein with insignificant endotoxin contamination. Recombinant human IL11 (2.8×10$^7$ U/ml) was a gift of Dr. Katherine Turner, Genetics Institute, Cambridge, Mass. Recombinant oncostatin M (1 mg/ml) was a gift of Dr. Philip Wallace, Bristol Myers, Seattle, Wash.

Soluble gp130

A soluble gp 130-immunoglobulin fusion protein (sgp130-Rg) was produced according to the procedure of Liu et al (Liu et al., Cytokine, 1994, 6:272–278) described in more detail below and was provided by Dr. Philip Wallace (Bristol-Myers Squibb, Seattle, Wash.).

The following method was used to construct the sgp130-Rg-Expression Plasmid. A cDNA clone encoding human gp130 was first digested with EcoR1 and the resulting 3' sticky end was filled in with DNA polymerase Klenow fragment in the presence of all four dNTP's followed by the ligation of BamH1 linkers (NEB. #1065). A 1.9 kb DNA fragment encoding the extracellular domain of gp130 (AA 1–606) was obtained by digesting this DNA with BamH1 and Xho1. This fragment was subcloned into a mammalian expression vector containing a genomic DNA fragment encoding the human IgG1 constant region as previously described.

The following method was used to purify the sgp130-Rg Protein. COS-7 cells were transfected with 3 µg/ml sgp130-Rg plasmid DNA by the DEAE-dextranchloroquine method. Twenty-four hours after transfection, the medium was changed to serum-free DMEM and collected after another 4 days. The soluble recombinant gp130 protein was purified from the media by protein A sepharose chromatography, analyzed and stored PBS at −20° C.

Hybridomas Producing Mabs to Human sgp130

BALB/c mice were immunized (bi-weekly × 3) with 20 µg sgp130/Rg by subcutaneous injection initially in complete Freund's adjuvant (Sigma Chemical Company, St. Louis, Mo.) and by subsequent intraperitoneal injection in PBS. Once a suitable titer of anti-gp130 activity was detected in the serum (see assay below), a final injection of 10 µg sgp130/Rg was given intravenously. Four days later, the splenocytes were obtained, fused with mouse myeloma cells [Sp/20; American Type Culture Collection (ATCC), Rockville, Md.] using PEG 1500, and hybrids were selected in HAT medium. Anti-gp130 Mabs were detected in expanded culture supernatants and sera as follows: 96 well microtiter plates were coated with sgp130/Rg fusion protein or IgG alone (100 µl of 2 µg/ml in PBS) and blocked with 1% bovine serum albumin (BSA) in PBS. Mouse sera or culture supernatants were added to each well, incubated for 2 hrs at 20° C. and bound antibodies subsequently detected with peroxidase-conjugated goat anti-mouse IgG (100 µl of 10 µg/ml in PBS supplemented with 1% BSA and 0.1% Tween 20).

Gp130 positive/Rg negative hybrids were sub-cloned twice by limiting dilution and expanded by intraperitoneal injection of Pristane-treated BALB/c mice. The IgG was purified from ascites fluid by Protein G chromatography (Pharmacia, Piscataway, N.J.). Antibody subtype was determined with a commercial isotype kit (Ab-Stat-I, Sangstat Medical Corporation, Menlo Park, Calif.). In some experiments, the Mabs were biotinylated. Antibodies were dialyzed into 50 mMborate buffer (pH 8.0) and incubated at a ratio of 1 mg protein/75 µg NHS biotin (from a fresh stock of 10 mg/ml in dimethylformamide) for 30 min at 37° C. Excess biotin was removed by gel filtration on a PD-10 column (Pharmacia).

Epitope Analysis

A competition ELISA was performed: sgp130 was bound to a microtiter plate at 0.5 µg/ml in PBS and blocked with 3% BSA. Biotinylated anti-gp130 and control Mabs (10 µg/ml) were added to each well in the presence and absence of each of the unlabelled anti-gp130 and control antibodies (10 µg/ml). Bound labelled antibody was detected with streptavidin-peroxidase (Vector).

Western blotting

SDS-polyacrylamide gel electrophoresis (SDS-PAGE) of nonreduced sgp130/Rg and biotinylated MW markers (Bio-Rad; Richmond, Calif.) was performed on 5% acrylamide gels. After electroblotting onto nitrocellulose and blocking with 1% BSA, individual lanes were cut out and incubated with 1 µg/ml of one of the 5 anti-gp130 Mabs. After thorough washing, Mabs binding gp130 were detected by incubation with alkaline phosphatase conjugated goat anti-rouse (Sigma).

Fibrinogen biosynthesis assays

Cytokine-stimulated fibrinogen production was measured in a human hepatoma cell line. Hep 3B cells (ATCC) were maintained at subconfluence in Iscove's medium supplemented with glutamine and penicillin/streptomycin (IMDM) and 10% fetal calf serum (FCS; Gibco, Grand Island, N.Y.). Prior to assay, cells were harvested by trypsinization, washed and transferred to 96 well microtiter culture plates and grown to near confluence. Cells were washed and treated in triplicate (in 2% FCS) with cytokines (0-100 ng/ml) and anti-gp130 Mabs (0–10 µg/ml). Culture supernatants were harvested and assayed for fibrinogen by ELISA. Microtiter plates were coated with rabbit anti-human fibrinogen IgG (Dako, Carpinteria, Calif.) at a dilution of 1:1000 in 0.1M carbonate/bicarbonate buffer, pH 9.6. Diluted samples and standards were applied to washed plates and bound fibrinogen detected with peroxidase-conjugated rabbit antihuman fibrinogen IgG (1:1000; Dako). The assay standard was pooled human plasma calibrated against a commercial fibrinogen standard (Sigma).

Melanoma cell (A375) growth inhibition assay

The assay was based upon the procedure of Horn et al (Horn et al., Growth Factors, 1990, 2:157–165). The IL-6-sensitive A375 melanoma cell line (a gift from Dr. Philip Wallace) was maintained at sub-confluency in IMDM with 10% FCS. For assay, cells were harvested by trypsinization, washed and plated in triplicate at 500 cells/well of a 96 well microtiter plate. Cells were cultured in the presence of cytokines (0–100 ng/ml) and anti-gp130 Mabs (0–10 µg/ml) until control wells (containing no cytokines or antibody) achieved confluence. The medium was then removed and cells were stained with 100 µl /well of crystal violet solution (0.1% in 20% methanol) for 30–60 min. The cells were then washed ×3 in PBS, the dye eluted with 100 µl/well of 0.1M sodium citrate, pH 4.2 in 50% ethanol and the OD$_{600}$ of the individual wells measured.

Cross-Reactivity of Mabs with Canine Cells

A. Antigenic localization

Human and dog peripheral blood mononuclear cells were isolated according to the procedure of Bauer et al (Bauer et al., *J. Exp. Med*, 1989, 170:1537–1549) with modifications. Diluted whole blood (1:2 in IMDM/10% FCS) was centrifuged over Ficoll-Hypaque to enrich for monocytes. A combination of light, scatter characteristics and reactivity to a Mab specific to the human myeloid marker CD14 (Mo-2, Coulter, Hialeah, Fla.) were used to define the monocytic population with a FACScan flow cytometer (Becton Dickinson; Mountainview, Calif.). Cross-reactivity of the anti-gp130 Mabs on canine monocytes was then assessed.

B. Functional Inhibition

To determine if the Mabs could block blood cell IgG production, peripheral blood mononuclear cells were cultured with pokeweed mitogen (PWM, 0.5 µg/ml; Sigma), IL-6 (10 ng/ml) and anti-gp130 Mabs (10 µg/ml) based upon a previously published method (Muraguchi et al., J. Exp. Med., 1988, 167:322–344), and assayed for dog IgG by ELISA.

In vivo Mab Administration

Dogs were given either 4 mg/kg Mab 2H4 or 4B11 twice a day by intravenous bolus infusion for 3–4 days. The dosage of antibody was chosen to ensure that serum levels would exceed those required in vitro to inhibit the biological activity of IL-6. One day after initiation of Mab infusion (at T=24 hours), IL-6 was given subcutaneously at 40 µg/kg/day daily for up to 10 days. This dose was previously shown to induce a number of systemic effects in dogs including a reproducible acute phase response. Control dogs received either IL-6 alone at the same dose or diluent buffer containing no IL-6 or Mab. Blood samples were drawn at regular intervals to monitor the acute phase response and peripheral blood cell counts.

C-Reactive Protein (CRP)

Ninety-six-well microtiter plates were coated with 100 µl of 5 µg/ml phosphorylcholine-derivatized keyhole limpet hemocyanin (PC-KLH; a gift of Dr. Larry Potempa, Immtech Corp, Chicago, Ill.), diluted in Tris-buffered saline, pH 7.4 (TBS) and incubated for 1–2 hrs at 37° C. After washing, TBS containing 2 mM $CaCl_2$ (TBS-Ca) was added, the plates were incubated for 1–2 hrs at 37° C., blocked with 1% BSA in TBS-Ca, followed by the addition of 100 µl/well of diluted test samples and standards in TBS-Ca. After additional incubation for 1–2 hrs at 37° C., bound dog CRP was detected with a Mab raised against human CRP cross-reacting with dog CRP (provided by Dr. L. Potempa). Bound antibody was detected with peroxidase-conjugated goat anti-mouse IgG (Sigma). Dog CRP (100–150 µg/ml) was used as a standard and was purified from 50 ml serum (obtained from a normal dog stimulated with 40 µg/kg/day IL-6 for 4 days) by affinity chromatography on phosphorylcholine-substituted Biogel A beads.

Erythrocyte Sedimentation Rate (ESR)

The ESR, primarily a reflection of fibrinogen concentration of the plasma, was performed according to standard methods (Bottinger et al., *Br. Med. J.*, 1967, 2:85–87)

Dog plasma fibrinogen

Dog plasma fibrinogen was measured by ELISA. Ninety-six-well microtiter plates were coated with rabbit anti-human fibrinogen IgG (Dako) at a dilution of 1:1000 in carbonate/bicarbonate buffer pH 9.6. Diluted samples and standards were applied to washed plates and bound fibrinogen was detected with a biotinylated Mab (2B11 or 2G7) raised against purified dog fibrinogen. Dog fibrinogen (4.3 mg/ml) purified as previously described (Heilmann et al., *Cytometry*, 1994, 17:287–293) was used to standardize the assay. Bound biotinylated antibody was detected by incubation with streptavidin-peroxidase.

Measurement of Infused Human IL-6

Plasma IL-6 levels in dogs were measured using a commercial ELISA kit (a gift from Incstar, Stillwater, Minn.) specific for human IL-6.

Measurement of Infused Murine Mab

Circulating levels of infused antibody in dogs were measured with an ELISA specific for mouse IgG. Microtiter plates were coated with goat anti-mouse IgG (1:1000; Sigma) in carbonate/bicarbonate buffer. After blocking with 1% BSA, samples and standards were applied to wells, incubated and detected with peroxidase-conjugated goat anti-mouse IgG (Sigma). The standards were serial dilutions of purified Mabs (2H4 or 4B11) to gp130.

Measurement of the canine humoral immune response to infused Mab

The immune response of the dogs to the Mab infusions was monitored by ELISA. Microtiter plates were coated with 2H4 or 4B11 at 10 µg/ml in PBS. After blocking with 1% BSA, diluted serum samples were applied to each well. Bound dog anti-mouse antibodies were detected with peroxidase-conjugated rabbit anti-dog IgG (affinity adsorbed with Mab-Sepharose).

Statistics

Data are expressed as the mean ± one standard deviation (SD). Significance was analyzed using the paired Student's t-test.

RESULTS

Hybridomas producing Mabs specific to spg130

Five hybridomas producing anti-gp130 Mabs as determined by ELISA were cloned and the Mabs purified by protein G chromatography. Isotype analysis of the purified antibodies showed that all 5 hybridomas (designated 3F7, 2H4, 1G1, 4B11, 5A8) were producing a single isotype ($IgG_1$). Epitope analysis suggested that 3F7, 4B11, 1G1 and 2H4 each reacted with a unique gp130 epitope. Western blotting after unreduced SDS-PAGE revealed that each antibody bound to sgp130/Rg which was previously shown to be a homodimeric molecule of approximately 260 kd.

Figure 1:
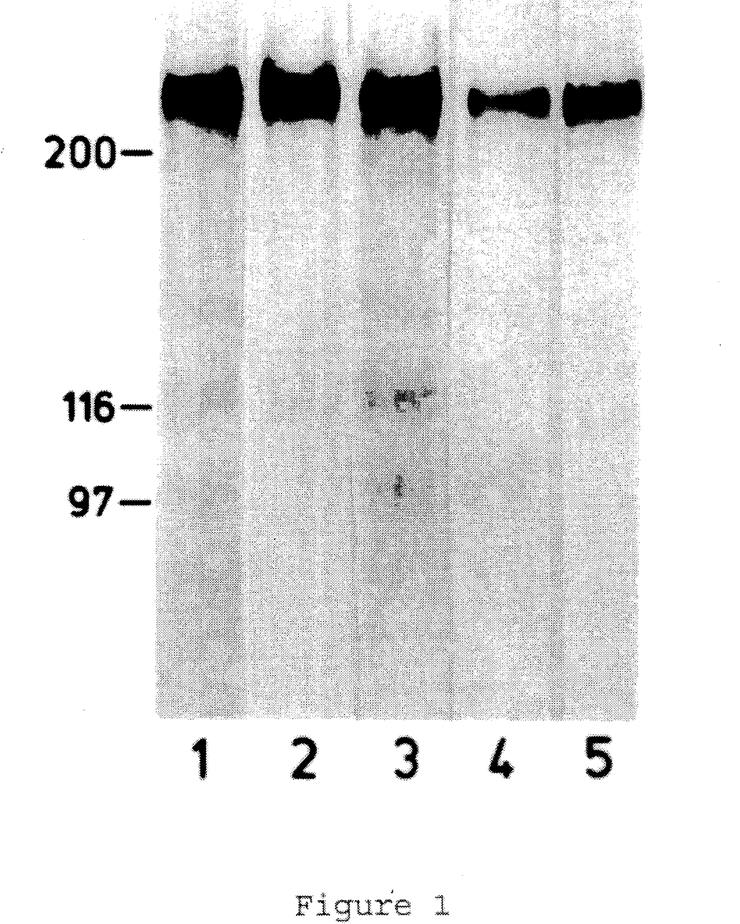
FIG. 1 is a Western blot showing the binding of five gp130 antibodies to spg130-Rg, the immunogen against which the antibodies were formed.

FIG. 1 is a Western blot showing the binding of the five gp130 Mabs to sgp130-Rg. Unreduced SDS-PAGE was performed on a 5% acrylamide gel followed by electroblotting onto nitrocellulose. After blocking, individual lanes were incubated with different gp130 Mabs (1 µg/ml) for 2 hrs prior to washing and incubation with 1 µg/ml goat anti-mouse IgG (alkaline phosphatase-conjugated). The blots were then incubated with alkaline phosphatase substrate. The Mr ($\times 10^{-3}$) of biotinylated standards is shown on the left. Lanes 1–5 are respectively Mabs, 2H4, 4B11, 3F7, 1G1, and 5A8.

Figure 2A:
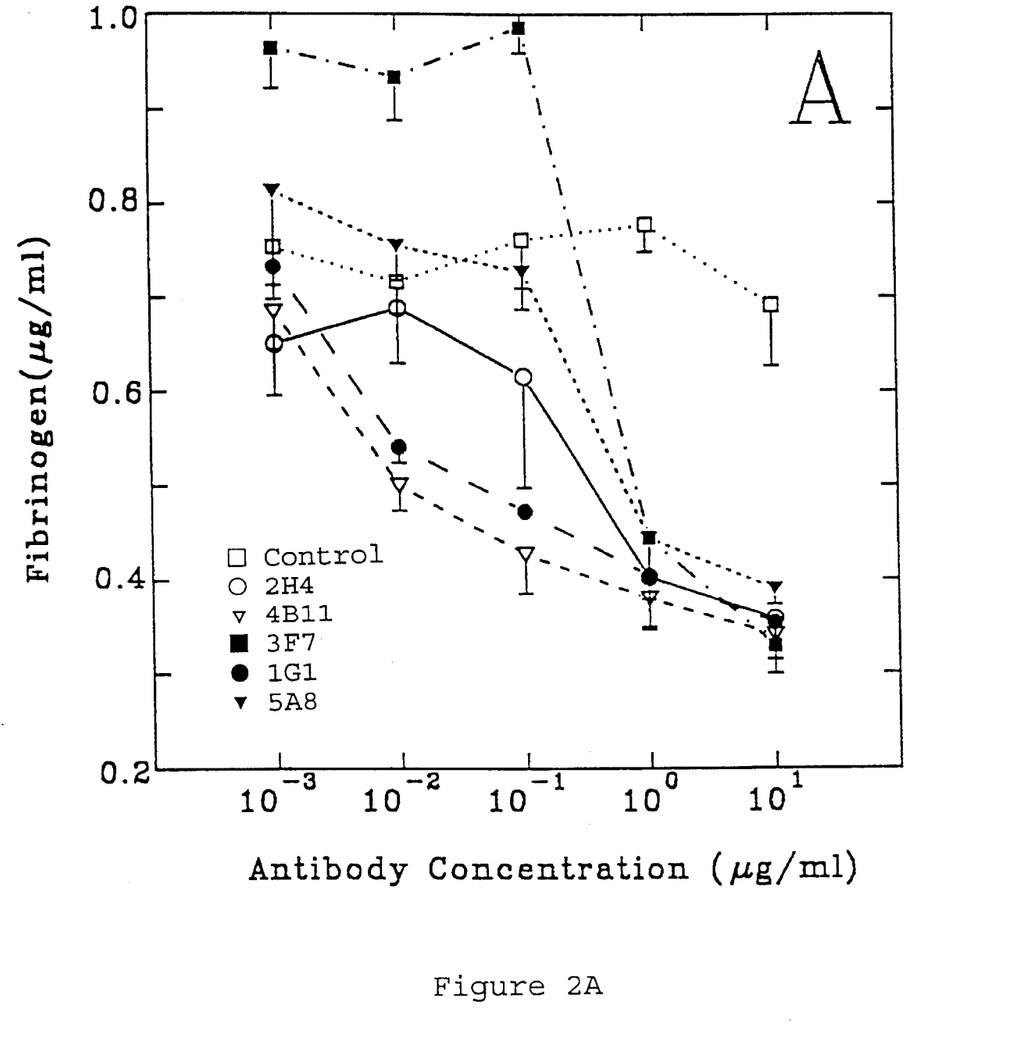
FIG. 2A is a graph showing the influence of the antibodies of the present invention against fibrinogen production in vitro in cells treated with IL-6.

IL-6 has been shown to induce the hepatic acute phase response in human hepatoma cell lines in vitro. Therefore, the influence of the five anti-gp130 Mabs (0.01–10 µg/ml) on fibrinogen synthesis induced by 2 ng/ml IL-6 was assessed. FIG. 2A shows the effects of various concentrations of the Mabs on fibrinogen synthesis at an intermediate stimulatory dose of 2 ng/ml of IL-6. Cells were cultured in triplicate with IL-6 and antibodies for 72 hours. Data are expressed as the mean fibrinogen concentration (µg/ml ± 1SD; ordinate). The concentration of the antibodies is shown on the abscissa. Mabs 4B11 and 2H4 were the most potent inhibitors, significantly effective at all concentrations down to 0.01 µg/ml ($P \leq 0.003$) but not at 0.001 µg/ml ($P > 0.05$). Mabs 5A8, 3F7 and 1G1 were only significantly effective at 1 and 10 µg/ml ($P \leq 0.001$).

Figure 2B:
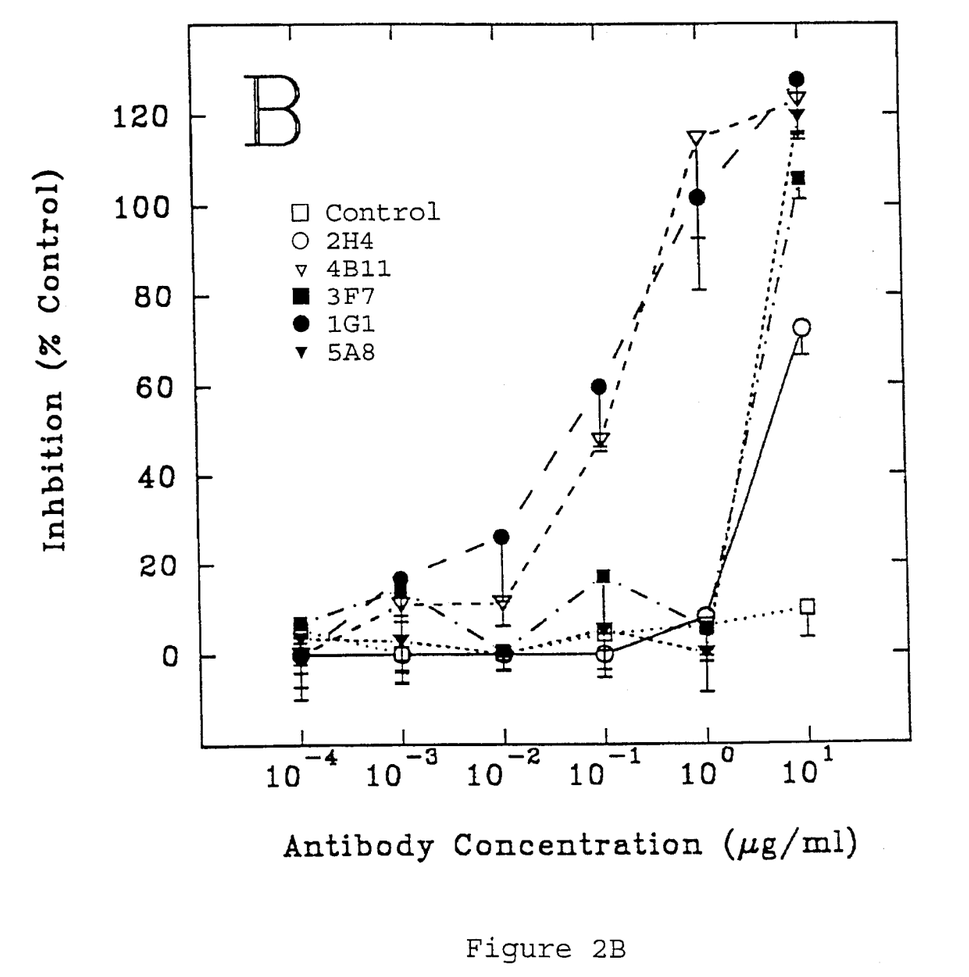
FIG. 2B is a graph showing the inhibitory influence of the antibodies of the present invention on the growth of A375 cells treated with IL-6.

IL-6 is also an inhibitor of growth of various tumor cell lines. Therefore, the influence of anti-gp130 Mabs (0.01–10 µg/ml; abscissa) on the inhibition of IL-6 (2 ng/ml)— induced growth of A375 cells was studied. A human melanoma cell line (A375) which is susceptible to IL-6-mediated growth inhibition was also employed (Horn et al., *Growth Factors*, 1990, 2:157–165). FIG. 2B shows the inhibitory influence of the gp130 Mabs on IL-6induced growth retardation of A375 cells. Cells were cultured in triplicate until control cells (cultured in the absence of Mabs) were confluent. Percentage inhibition (±1SD) is expressed on the ordinate as a function of control values. As shown in FIGS. 2A, Mabs 2H4 and 4B11 were the most potent inhibitors with significant inhibition observed as low as 0.01 µg/ml ($P \leq 0.001$ at 1 and 10 µg/ml, <0.005 at 0.1 µg/ml and <0.04 at 0.01 µg/ml, respectively). Mabs 5A8, 1G1 and 3F7 were inhibitory but only at the highest concentration of 10 µg/ml ($P<0.001$).

Influence of Anti-gp130 Mabs on IL-11 and Oncostatin M Activities

As anti-gp130 Mabs have previously shown to be effective at inhibiting other members of the family of gp-130 signalling cytokines, the potential inhibitory influence of these new Mabs on IL-11 and Oncostatin M (used at 0.01–100 ng/ml) was investigated. Mabs 3F7, 2H4 and 4B11 (each used at 2 µg/ml) were all inhibitors of Hep3B fibrinogen synthesis (e.g., 84%, 60% and 67% reduction in fibrinogen respectively, at 100 ng/ml IL-11; $P<0.03$). However, of the 5 Mabs (all used at 2 µg/ml), only 4B11 was a significant inhibitor of Oncostatin M bioactivity on A375 cells (e.g., 50% inhibition when 2 ng/ml Oncostatin M was used). At all concentrations of Oncostatin M tested (except 0.01 ng/ml), the inhibitory effect was significant ($P<0.05$).

Influence of anti-gp130 Mabs on Canine Cells

The above results suggested that 2H4 and 4B11 were the best in vitro inhibitors of gp130-signalling cytokines. To utilize these antibodies in an established in vivo canine model, it was necessary to determine if the Mabs cross-reacted with dog cells and were capable of inhibiting signal transduction. Both 2H4 and 3F7 cross-reacted with dog monocytes in a flow cytometric assay with a similar fluorescence intensity as was noted with human cells. To determine if the Mabs were capable of functional inhibition of canine cells, they were tested in a dog peripheral blood cell IgG assay in the presence of pokeweed mitogen (PWM) and IL-6 (Muraguchi et al., *J. Exp. Med.*, 1988, 167:322–344). The effects of three Mabs (at 10 µg/ml) on IgG synthesis were studied in the presence of 10 ng/ml IL-6 and 0.5 µg/ml of PWM. Mabs 2H4, 4B11 and 3F7 were observed to inhibit dog B cell IgG synthesis from 32–58%. This degree of cross-reactivity of these antibodies with canine cells suggested their potential for investigation of in vivo efficacy in these animals.

In vivo Inhibition of the IL-6-Stimulated Canine Acute Phase Response

Figure 3A:
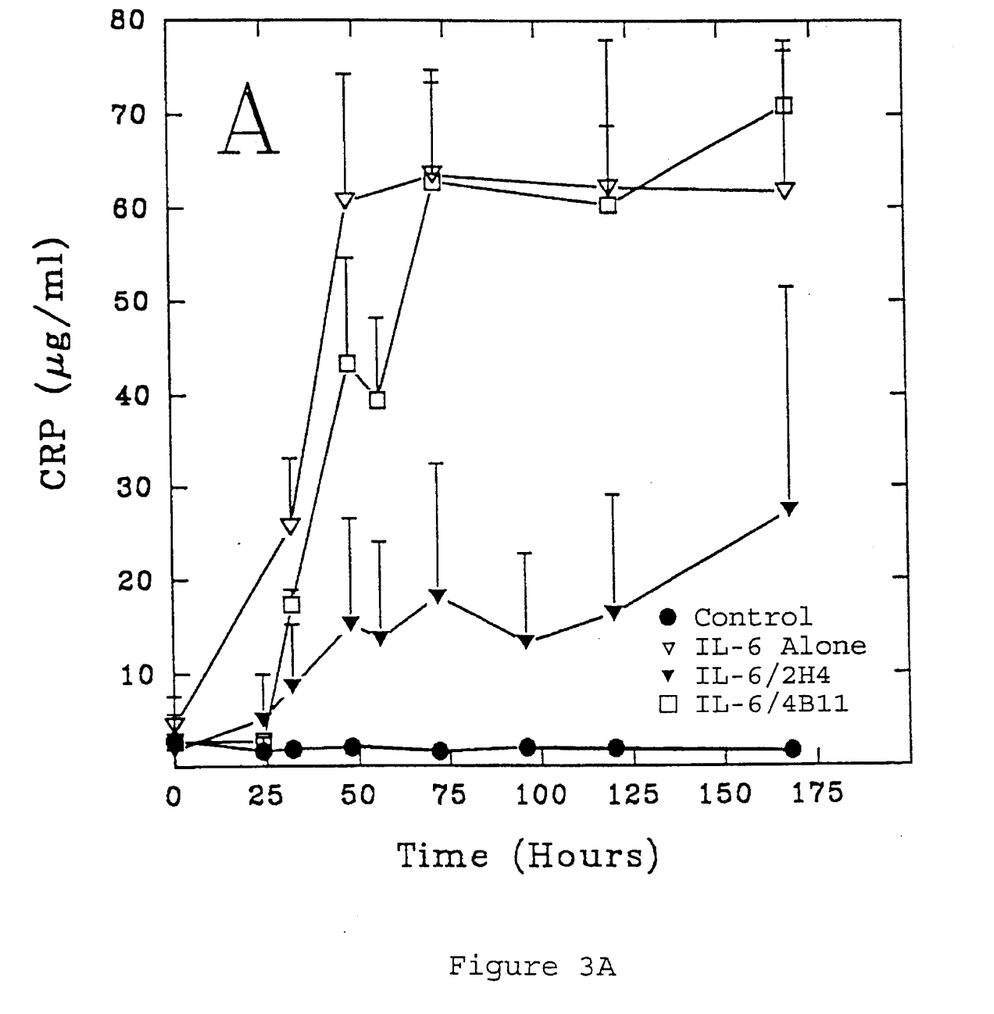
FIG. 3A is a graph showing the effects of the 2H4 and 4B11 antibodies of the present invention on C-reactive protein concentration in dogs with IL-6-induced acute phase response.
Figure 3B:
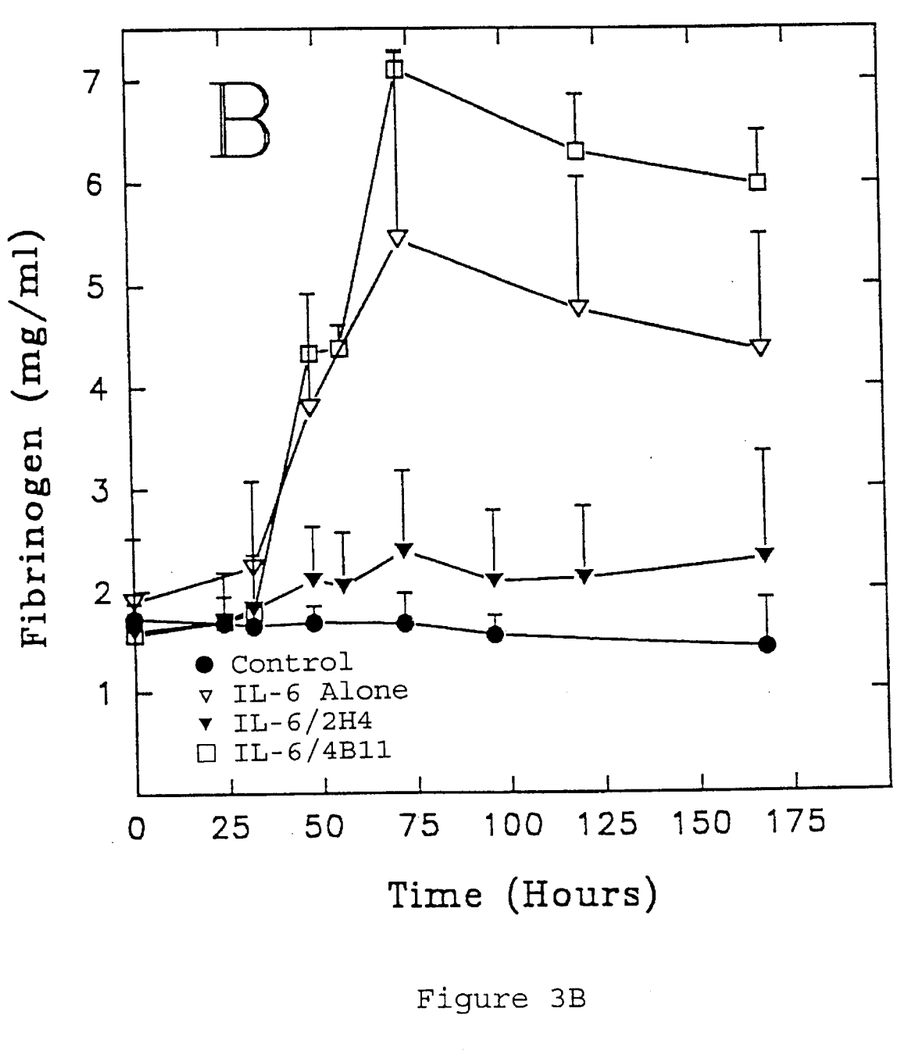
FIG. 3B is a graph showing the effects of the 2H4 and 4B11 antibodies of the present invention on fibrinogen concentration in dogs with IL-6-induced acute phase response.

FIGS. 3A and 3B show the influence of 8 mg/kg/day of 2H4 on the acute phase response induced by 40 µg/kg/day of IL-6 compared with control dogs, dogs receiving IL-6 alone and dogs receiving 4B11 and IL-6. The 2H4 data are expressed as the mean ± 1SD of three identical experiments. The 4B11 data are from one experiment. The abscissa indicates time in hours where T=0 is the sample taken immediately prior to the first injection of antibody and T=56 is the last injection. IL-6 was begun at T=24 and continued for 10 days. The ordinates represent the concentrations of either CRP (µg/ml) or fibrinogen (mg/ml) in the plasma.

No discernible adverse effects during treatment of any of the dogs were observed. IL-6 alone resulted in a rapid and significant elevation ($P<0.01$) of plasma CRP levels above control levels at 8 hours following initial administration of IL-6 (i.e., at T=32 hrs on FIG. 3A), rising to a plateau of 60 µg/ml 24 hours after injection of IL-6 (i.e., at T=48 hrs on FIG. 3A; all samples $P<0.01$ compared with control). The plasma fibrinogen response (FIG. 3B) was slower and less marked than that of CRP (no significant difference compared with control at T=32 hours (8 hours after IL-6 injection; $P>0.2$), but ultimately increased ~3-fold, attaining a maximum level of 5.45 mg/ml at T=72 hours (48 hours after IL-6 injection; all samples were significantly greater than control levels from T=48 hours onwards; $P<0.05$). Infusion of 2H4 resulted in the abrogation of the IL-6-induced CRP and fibrinogen responses (no significant difference from control levels at all time points; $P>0.1$). Mab 4B11 appeared to be totally ineffective at inhibiting the IL-6-induced response (n=1) as measured by CRP and fibrinogen production. Measurement of the ESR at 96 hours in two of the three experiments revealed marked elevations in the IL-6-treated dogs (48 mm and 35 mm, respectively) compared to either control (1 mm in both) or IL-6 plus 2H4-treated animals (3 mm and 1 mm, respectively; $P<0.03$). These results correlate well with plasma fibrinogen levels at those time points at which the ESRs were determined.

Measurement of plasma IL-6 by ELISA prior to the last antibody infusion (i.e. on day 4) confirmed that all dogs receiving either IL-6 alone or IL-6/2H4 had levels of human IL-6 in their peripheral blood that were not significantly different (155.9±141.4 pg/ml and 73.1±37.7 pg/ml, respectively; $P>0.3$). IL-6 in control samples (i.e., dogs not given IL-6) was undetectable.

Figure 4:
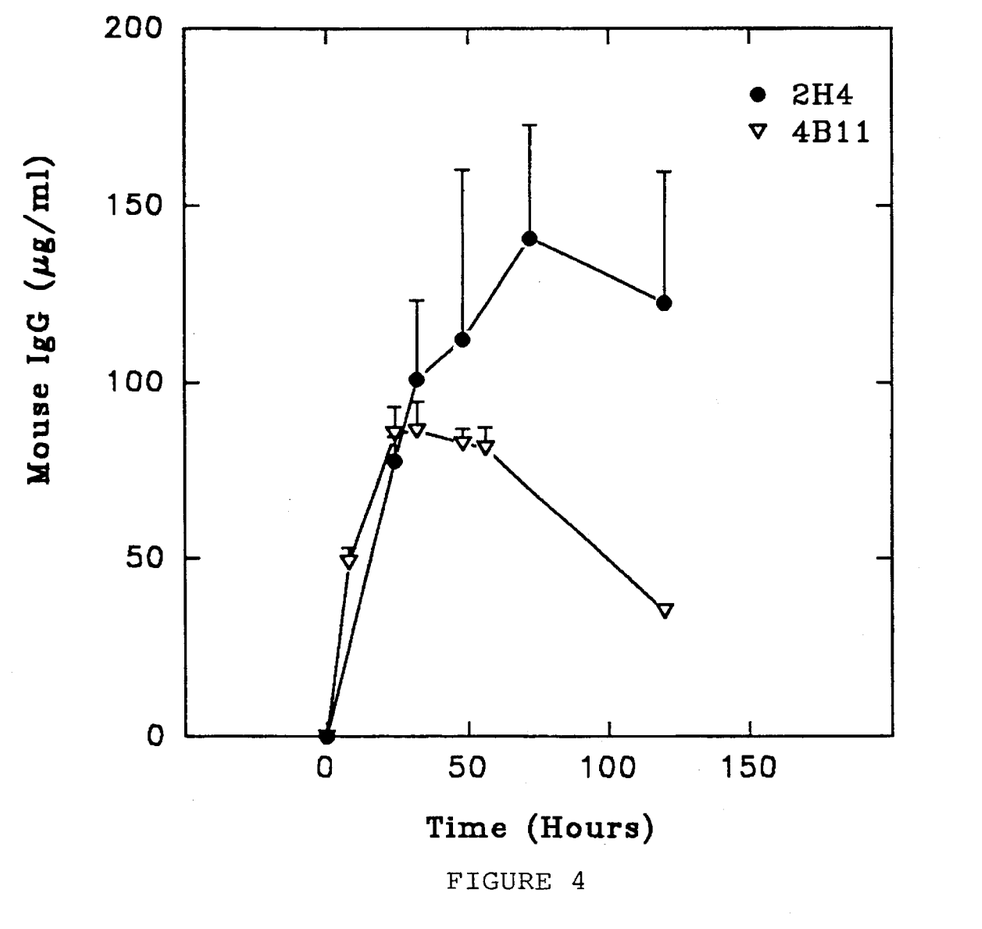
FIG. 4 is a graph showing levels of circulating mouse IgG in dogs treated with the 2H4 and 4B11 antibodies of the present invention.

FIG. 4 shows that comparable levels of circulating mouse IgG were detected in the plasma samples from all 4 experiments in animals treated with 2H4 or 4B11. There was no significant difference between the mouse IgG levels in the 4B11 dog compared to the three 2H4-treated dogs during the initial IL-6 induction of the acute phase response. As 4B11 was only infused for 3 days (i.e., up to 56 hours on FIG. 4) there is a significant difference in the decay of IgG levels in the later 4B11 samples when compared to the 2H4 dogs.

Influence of 2H4 on platelet counts

One of the in vivo effects of IL-6 administration is the augmentation of the peripheral blood platelet count (Ishibashi et al., *Blood*, 1989, 74:1241–1244). Table 1 shows that 2H4 abrogated this influence of IL-6 on thrombocytopoiesis. After the antibody infusion was discontinued, there was a significant delay in the rise in the platelet count in all 3 dogs, indicating that suppression of IL-6-induced thrombocytopoiesis was antibody-mediated. In contrast, infusion of 4B11 had no significant effect on the platelet count when compared to the IL-6 control.

TABLE 1

| | Platelet Count/µl × 10⁻³ | | | | | | | |
|---|---|---|---|---|---|---|---|---|
| | EXP1 | | EXP2 | | EXP3 | | EXP4 | |
| Time (days) | IL-6 | IL-6/2H4 | IL-6 | IL-6/2H4 | IL-6 | IL-6/2H4 | IL-6 | IL-6/4B11 |
| 0 | 275 | 297 | 492 | | 204 | 222 | 241 | 292 |
| 1 | 287 | 303 | 471 | 308 | 181 | 184 | 249 | 315 |
| 2 | | | 431 | 294 | | | | |
| 3 | 299 | 321 | | | | | 239 | 283 |
| 4 | | | 450 | 304 | 157 | 173 | | |
| 5 | 423 | | | | | | | |
| 6 | | | 585 | 274 | | | 328 | 322 |
| 7 | | | | | 326 | 187 | | |
| 8 | 518 | 311 | 483 | | | | 329 | 384 |
| 9 | | | | | 440 | 220 | | |
| 10 | 456 | 378 | | | | | 334 | 424 |
| 11 | | | 569 | 235 | 462 | 213 | | |
| 12 | 503 | 468 | | | | | | |
| 13 | | | | | | | | |
| 14 | | | 558 | | | | 406 | 453 |
| 15 | | | | | 486 | 358 | 448 | 506 |
| 16 | | | 575 | | | | | |
| 17 | 450 | 344 | | 344 | | | 366 | 500 |
| 18 | | | | | | | | |
| 19 | | | 583 | | | | | |

Table 1. Platelet counts of dogs treated with IL-6 alone (n = 4), IL-6/2H4 (n = 3) or IL-6/4B11 (n = 1). IL-6 was given from day 1 until day 11. Mabs were infused from day 0 until day 3.

The results shown above indicate that Mab 2H4 is an effective in vivo inhibitor of the acute phase response to IL-6. The 2H4 Mab not only abrogated the observed rise in CRP and fibrinogen levels but also delayed IL-6-induced augmentation of the platelet count. 4B11 was ineffective at the same dosage as 2H4 even though 4B11 was shown to inhibit IL-6 bioactivity on both human and canine cells in vitro to a similar degree as 2H4. The in vivo failure of 4B11 was not related to its biological availability since identical amounts were infused and the post-transfusion serum concentrations of both 2H4 and 4B11 were similar during the initial induction period of the acute phase response (FIG. 4).

Trestment of Rheumatoid Arthritis

As noted above, IL-6 has been implicated in the immunopathogenesis of rheumatoid arthritis as well as in chronic inflammation. In view of the effects of Mab 2H4 in vivo in inhibiting the acute phase response in dogs, as noted above, it is proposed herein that Mab 2H4 would be effective in ameliorating rheumatoid arthritis effects in humans.

In one proposed method of treatment, patients would be examined for clinical signs of inflammation (e.g. tenderness, swelling, redness, and range of motion). The inflamed joint is then prepared for intra-articular injection with iodine application. Aspirates of joint fluid would be obtained prior to injection to measure IL-6, C-reactive protein, and inflammatory cells (neutrophils, monocytes and lymphocytes) as an objective measure of disease activity. Treatment is provided as an injection of 10 mg of Mab 2H4 into the articular cavity by slow push. The clinical course following injection is followed, in particular with attention paid to decrease in pain, swelling and redness. Aspirates of joint fluid may be obtained three days following injection for measurement of IL-6, C-reactive protein, and inflammatory cells as an objective measure of efficacy. Injections may be repeated once a month up to three times. Blood and joint fluid will be assessed during the course of therapy for development of anti-murine antibodies and for levels of IL-6 and C-reactive protein. Preferably, the 2H4 antibody will be "humanized" prior to use in human therapeutic treatment using methods which are well known to one of ordinary skill in the art, see for example, Masuho, Y., Biotechnology, 20:405–30, 1992; Sato et al., Molecular Immunology, 31(5):371–81, 1994; and Co et al., Proc. Natl. Acad. Sci. USA, 88:2869–73, 1991.

Treatment of Multiple Myeloma

As noted above, IL-6 has also been implicated in the pathogenesis of multiple myeloma. The 2H4 antibody is proposed for use in treating patients with, for example, refractory multiple myeloma (defined as unresponsive to chemotherapy). Prior to treatment, measurements in the patient would be made for complete blood count, fibrinogen level, C-reactive protein, calcium level, and quantitative serum immunoglobulin levels. Urine would be obtained for immunoglobulin and light chain levels. A bone marrow aspiration and biopsy would be performed to assess plasma cell percentage. Patients would be given 2 mg/kg/day of Mab 2H4 diluted in normal saline by slow intravenous injection. This would be repeated every other day until or unless no further clinical response was noted. Four days after treatment, blood studies would be assessed to evaluate efficacy. Percentage of plasma cells in the bone marrow would be evaluated at two weeks and four weeks after treatment. Treatment outcome would be determined by changes in serum/urine immunoglobulin levels, clinical response (e.g., changes in pain, and skeletal x-ray alterations) alterations in plasma cell infiltration of the marrow, and by changes in blood counts and calcium levels. As noted above, preferably, the Mab 2H4 utilized in the present treatment would be of a "humanized" type.

Measurement of Soluble GP-130

Soluble receptors such as soluble gp-130 represent truncated forms of membrane-bound receptors lacking their transmembrane and cytoplasmic domains and still exhibiting cytokine-binding abilities with affinities similar to their membrane-bound counterparts. Soluble receptors compete with their membrane-bound forms for binding of free cytokines. As a result, most soluble receptors inhibit the biologic activity of specific cytokines. For this reason, it may be useful to detect the levels of soluble gp130. The present invention contemplates a method of using either Mabs 2H4 or 4B11 to detect levels of soluble gp130. The following details the specific steps in a conventional sandwich ELISA assay for detecting sgp130.

1) Coat ELISA plates with 100 µl of 2 µg/ml 2H4 or 4B11 anti-gp130 Mabs diluted in carbonate buffer pH 9.6 (1.59 g of anhydrous sodium carbonate and 2.93 g of sodium hydrogen carbonate, 0.2 g Sodium azide in 1 litre of distilled water and stored at room temperature (RT). Seal plate and incubate for at least 1 hour at room temperature or overnight at 4° C. in a moisture chamber.

2) Wash plates with filter sterilized PBS/Tween+3 (fill wells up to the brim). (10 mM PBS/Tween—0.345g of sodium dihydrogen orthophosphate, 2.68 g di-sodium hydrogen orthophosphate dodecahydrate, 8.474 g sodium chloride, 1 ml of Tween 20, pH 7.2 in 1 litre of distilled water, store at RT).

3) Block all wells with 250 µl/well of 2% BSA in above washing buffer (use same buffer through entire assay)—incubate for 1 hour at RT or overnight at 4° C. in a moisture chamber. Plates can be stored at this stage.

4) Wash with buffer X3 as above.

5) Dry plates before applying samples.

6) Apply Blanks, standards and unknowns diluted in wash buffer containing Tween (as above).

Blank: Provide 100 µl of dilution buffer alone in the first column.

Standards: Provide 2 µg/ml of sgp130Rg double diluted downwards in wash buffer to give a standard curve with 7 points in duplicate (2, 1, 0.5, 0.25, 0.125, 0.0625 and 0.03125 µg/ml).

Samples: Provide human sera/plasma: dilute by factors of ½, ¼, ⅛ and 1/16.

7) Incubate for 1 hour at ambient room temperature in moisture chamber.

8) Wash × 3 as above.

9) Apply second antibody (different from the capture Mab, such as Mab 3F7 biotinylated) 100 µl/well of 5 µg/ml Mab in wash buffer.

Biotinylation procedure: Apply 2 mls of Protein G purified Mab to a PD10 column pre-equilibrated in Borate buffer pH 8.0. Collect peak. Make up fresh NHS-Biotin: -20 mg/ml in DMF. Measure OD 280 of Mab peak and add 0.25 mg biotin/mg protein. Incubate for 30 minutes at 37° C. Dialyse overnight into 5 litres of PBS pH 7.2, or collect void fraction from another PD-10 column pre-equilibrated in PBS. Measure OD 280 nm.

10) Incubate for 1 hour at RT.

11) 30 minutes into above incubation prepare Sreptavidin-Peroxidase complex (Vector—ABC kit) in wash buffer (see kit instructions—usually 90 µl of A and 90 µl of B in 10 mls of wash buffer) and incubate for 30 minutes.

13) Wash plate × 3.

14) Add 100 µl/well and incubate for 1 hour.

15) Wash plate × 2 in wash buffer (same as above).

16) Wash plate × 1 in citrate buffer. (7.3 g of anhydrous citric acid and 23.87 g of disodium hydrogen orthophosphate pH 5.0 in 1 litre of distilled water).

17) Make peroxidase substrate. Two tablets of OPD (Sigma) in 50 mls of citrate buffer and add 50 µl of hydrogen peroxide stock. Let tablets dissolve fully before adding hydrogen peroxide.

18) Add 100 µl of substrate/well of ELISA plates. Pipette quickly from left to right on the plate assuming standards are on the left side.

19) Monitor OD 492 nm in the ELISA reading until top standard (2.0 µg/ml) reaches and OD of approximately 0.2.

20) Stop all wells with 50 µl of 1M sulphuric acid. Ensure that plate is pipetted identically as with the substrate to ensure that each well has identical incubation time.

21) Read plate at 492 nm and calculate results.

Changes may be made in the construction and the operation of the various components, elements, compositions and assays described herein or in the steps or the sequence of steps of the methods described herein without departing from the spirit and scope of the invention as defined in the following claims.

What is claimed is:

1. An antibody which specifically binds to the extracellular domain of human cytokine receptor gp130 and which is produced by a hybridoma having ATCC Accession No. HB12022.

2. A composition comprising the antibody of claim 1 suspended in a pharmaceutically acceptable carrier.

3. The antibody of claim 1 labeled with a detectable marker.

4. A hybridoma which produces antibody molecules that specifically bind to the extracellular domain of human cytokine receptor gp130, said hybridoma having ATCC Accession No. HB12022.

\* \* \* \* \*

UNITED STATES PATENT AND TRADEMARK OFFICE
CERTIFICATE OF CORRECTION

PATENT NO. : 5,571,513
DATED : November 5, 1996
INVENTOR(S) : Burstein

It is certified that error appears in the above-indentified patent and that said Letters Patent is hereby corrected as shown below:

Title page, PUBLICATIONS, after "Galfre" please add --et al.--.

Column 1, line 32, please delete "via common" and substitute therefor --via a common--.

Column 2, line 54, please delete "coliris" and substitute therefor --colitis--.

Column 3, line 50, please delete "Praklawn DR" and substitute therefor --Parklawn Dr--.

Column 5, line 2, please delete "IL11" and substitute therefor --IL-11--.

Column 6, line 19, please delete "rouse" and substitute therefor --Mouse IgG--.

Column 6, line 60, please delete "Antiqenic" and substitute therefor --Antigenic--.

Column 6, line 66, please delete ",".

Column 11, line 42, please delete "Trestment" and substitute therefor --Treatment--.

UNITED STATES PATENT AND TRADEMARK OFFICE
CERTIFICATE OF CORRECTION

PATENT NO. : 5,571,513
DATED : November 5, 1996
INVENTOR(S) : Burstein

It is certified that error appears in the above-indentified patent and that said Letters Patent is hereby corrected as shown below:

Column 13, line 15, please delete "+3" and substitute therefor --x3--.

Signed and Sealed this

Eighteenth Day of February, 1997

Attest:

BRUCE LEHMAN

Attesting Officer

Commissioner of Patents and Trademarks